United States Patent [19]

Lévai et al.

[11] 4,160,035

[45] Jul. 3, 1979

[54] PLANT PROTECTING AGENTS AND METHODS FOR THEIR USE

[75] Inventors: László Lévai; Gyula Mikite, both of Budapest; Attila Kis-Tamás, Pilisvörösvár, all of Hungary

[73] Assignee: Egyt Gyogyszervegyeszeti Gyar, Budapest, Hungary

[21] Appl. No.: 848,351

[22] Filed: Nov. 3, 1977

Related U.S. Application Data

[62] Division of Ser. No. 811,901, Jun. 28, 1977.

[30] Foreign Application Priority Data

Jul. 6, 1976 [HU] Hungary .............. EE 2430

[51] Int. Cl.² .............. A01N 9/24
[52] U.S. Cl. .............. 424/311; 424/308; 424/312; 560/105; 560/106; 560/254; 260/410.5
[58] Field of Search .............. 424/312, 313, 311; 560/105, 106, 254; 260/410.5

[56] References Cited

U.S. PATENT DOCUMENTS 3,274,236  9/1966  Schmerling .............. 560/228
3,970,759  7/1976  Frankenfeld et al. .............. 424/313

Primary Examiner—V. D. Turner
Attorney, Agent, or Firm—Young & Thompson

[57] ABSTRACT

A plant protecting composition with pesticidal effects contains an effective amount of at least one compound of the formula

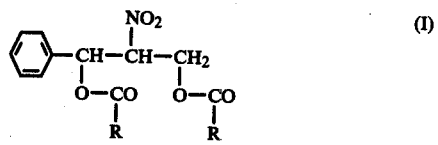

wherein R is a $C_{1-20}$ alkyl group or a phenyl or phenyl-$C_{1-3}$ alkylene group having optionally one or more $C_{1-3}$ alkyl or halogen substituents on the phenyl ring, and a diluent in an amount necessary to make up the final weight of the composition. To kill plant pests, the composition is applied to growing plants either prior to or after emergence.

2 Claims, No Drawings

PLANT PROTECTING AGENTS AND METHODS FOR THEIR USE

This is a division of application Ser. No. 811,901, filed June 28, 1977.

This invention relates to novel plant protecting agents, and to methods for their use. The active compounds of the plant protecting agents according to the invention are, with the exception of one derivative, novel substances.

Threo-1-phenyl-2-nitro-1,3-propanediol diacetate, the only known member of the active compounds, is an intermediate produced in the synthesis of chloramphenicol. According to the known method this compound is prepared by reacting cinnamic acetate with sodium nitrite and treating the resulting DL-erythro-1-phenyl-nitroso-2-nitro-3-acetoxy-propane with acetic anhydride in sulfuric acid (Chem. Abstr. 50, 6360 /1956/). No biological effect was attributed to this compound. Owing to the stereochemistry of the reactants applied the known process enables one to prepare the threo isomer only.

The novel plant protecting agents according to the invention contain one or more nitroalkanol derivative(s) of the general formula (I)

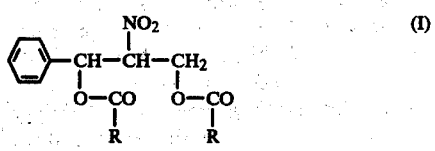

wherein R is a $C_{1-20}$ alkyl group or a phenyl or phenyl-$C_{1-3}$ alkylene group having optionally one or more $C_{1-3}$ alkyl or halogen substituent(s) on the phenyl ring.

The compounds of the general formula (I) have two centres of asymmetry (the carbon atoms in positions 1 and 2), consequently they exist in the form of two diastereomeric pairs (racemic erythro and threo compounds), which can be resolved further to yield the respective optically active laevorotatory and dextrorotatory compounds. Thus the total number of isomers amounts to four. Of the compounds having the general formula (I) the threo isomer of the R=methyl derivative is known.

The plant protecting agents according to the invention may contain one or more compound(s) of the general formula (I) as active principle, optionally in admixture with certain other known plant protecting substances. The total active agent content of the plant protecting compositions amounts to 0.01 to 96%. Beside the active agents, the compositions contain usual additives, such as solvents, carriers, diluents, extenders, dispersing agents, surfactants, agents modifying the duration of the effect, stickeners and/or stabilizers, in an amount necessary to make up the final weight (100%) of the composition.

The active compounds of the general formula (I) may be formulated into usual agricultural compositions, such as solutions, emulsions, suspensions, powders, dispersible powders, spray powders, wettable powders, foams, pulps, granulates, aerosols, emulsifiable concentrates, suspension concentrates, compositions for seed dressing, etc. Of these compositions the wettable powders (WP), emulsifiable concentrates (EC), colloidal suspension concentrates (Col.), microgranulates and sprays are particularly preferred.

The compositions are prepared according to methods known per se, such as by admixing the active compounds with carriers (e.g. liquid solvents, liquified gases and/or solid carriers) optionally in the presence of surfactants (e.g. emulsifying agents and/or dispersing agents) and/or foaming agents. If water is applied as solvent, organic liquids can also be admixed with the composition as co-solvents.

As solvents or liquid carriers e.g. the following substances can be applied: aromatic compounds, such as xylene, toluene or alkylnaphthalene, chlorinated aromatic compounds, such as chlorobenzene, chlorinated aliphatic hydrocarbons, such as methylene chloride or ethylene chloride, aliphatic hydrocarbons, such as paraffin hydrocarbons, alicyclic hydrocarbons, such as cyclohexane, alcohols, such as butyl alcohol or glycol, ethers and esters of said alcohols, ketones, such as acetone, methyl-ethyl-ketone or cyclohexanone, polar organic solvents, such as dimethyl formamide or dimethyl sulfoxide, furthermore water.

As liquified gases e.g. liquified propellants for aerosol compositions, such as halogenated hydrocarbons, furthermore liquified butane, propane, nitrogen and carbon dioxide can be applied. Of the solid carriers the following substances are to be mentioned: natural rock flours, such as kaoline, clay minerals, talc, chalk, quarz, montmorillonite or diatomaceous earth, and synthetic rock flours, such as highly disperse silicic acid, aluminium oxide and silicates. In the preparation of granular compositions first of all the following solid carriers can be applied: crushed and fractionated natural rocks, such as calcite, marble, pumice stone, sepiolite and dolomite, furthermore flours of organic origin, such as ground tobacco stalk, ground coconut shell, etc. As emulsifying and/or foaming agents non-ionic and anionic substances, such as polyoxyethylene-fatty acid esters, polyoxyethylene-fatty alcohol ethers (e.g. alkyl-aryl-polyglycol ethers), alkylsulfates, alkylsulfonates, arylsulfonates and hydrolyzed proteins can be applied. Of the dispersing agents the following are to be mentioned: lignin, sulfite waste liquors and methyl cellulose.

The compositions may also contain stickening agents, such as carboxymethyl cellulose or powdery, granular or latex-like polymers of natural or synthetic origin (e.g. gum arabic, polyvinyl alcohol or polyvinyl acetate).

If desired, dyestuffs, such as inorganic pigments, furthermore trace elements, such as salts of boron, iron, copper, cobalt, manganese, molybdenum and zinc, can also be admixed with the active agents.

The compositions according to the invention can be applied onto the area to be treated either as such or after diluting them to the appropriate final concentration. In order to facilitate handling, transporting and storage it is preferred to prepare the compositions in the form of concentrates which can be diluted to the required final concentration directly before application.

The active agent contents of the compositions ready for use may vary within wide limits. These compositions may contain 0.000001 to 96% by weight, preferably 0.01 to 10% by weight, of active agent. The compositions are applied onto the area to be treated according to known techniques, such as spraying, watering, etc.

The active agents of the general formula (I) are prepared by reacting 1-phenyl-2-nitro-1,3-propanediol of the formula (II)

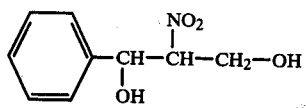

or an alkali metal salt thereof with an appropriate acylating agent.

This method is virtually simple; in practice, however, several difficulties arise when substances structurally similar to that of the formula (II) compound are to be acylated. These difficulties can be attributed partly to the aldol character of the compound and partly to the presence of the nitro group. Among others, the presence of a nitro group precludes the applicability of basic acid binding agents in the acylation procedure, since otherwise the nitro group undergoes a tautomeric rearrangement and the epimeric nitronic acid derivative forms. Furthermore, upon the effect of basic agents an aldol equilibrium takes place in the reaction mixture, the "retroaldol" component of which leads to the dissociation of the molecule. Moreover, 1-phenyl-2-nitro-1,3-propanediol is, like other nitro alcohols, a compound so highly liable to decomposition that no base is required to split off the loose proton attached to the carbon atom in position 2. In other words, the basicity of the solvent (such as aqueous alcohol) is already sufficient to initiate the decomposition process. In the solutions of 1-phenyl-2-nitro-1,3-propanediol a considerable degree of decomposition can be detected even upon standing at room temperature for some hours; and the rate of decomposition increases abruptly upon raising the temperature. When examining the formation and decomposition processes of 1-phenyl-2-nitro-ethane-1-ol, a compound structurally very similar to 1-phenyl-2-nitro-1,3-propanediol, it has been stated that this compound cannot be acylated at all (Gazz. Chim. Ital. 79, 192–201 /1949/). This fact can be fully explained by the factors discussed above.

Based on the above one could not conclude that 1-phenyl-2-nitro-1,3-propanediol can be acylated at all, and no such procedure has been described so far in the literature, either.

Now it has been found, unexpectedly, that the acylated nitro compounds of the general formula (I) can be prepared from the formula (II) compound quite easily and without the occurrence of side reactions when either of the isomeric forms (erythro or threo) or an isomeric mixture of 1-phenyl-2-nitro-1,3-propanediol or an alkali metal salt thereof is reacted with an acylating agent under mild conditions. As acylating agent preferably an acyl halide or an acid anhydride is applied. The reaction can be performed either in the presence or in the absence of solvent media. When an alkali metal salt (preferably the sodium salt) of 1-phenyl-2-nitro-1,3-propanediol is applied as starting substance, it is particularly preferred to perform the reaction with an acyl halide in a solvent, such as in acetic acid, at a temperature about 40° C. The reaction requires about 8 hours. In this way a mixture of erythro and threo isomers, containing the two isomeric forms in a ratio of about 1:1, is obtained with a good yield. The isomeric mixture can be separated into the pure isomers by crystallization.

It is also preferable to start with the pure erythro or threo isomer of 1-phenyl-2-nitro-1,3-propanediol and to perform the reaction without adding any further solvent to the mixture. In this instance the corresponding pure erythro or threo isomer of the acylated compound is obtained with good yields.

According to a further preferred method an acid anhydride is applied as acylating agent, and the reaction is performed without applying a solvent, in the presence of a catalytic amount of a mineral acid or the chloride of the anhydride. Of course, the reaction can also be performed with a mixture of the appropriate acyl halide and acid anhydride.

The formula (II) compound used as starting substance in the process of the invention is an easily available, known substance. The sodium salt can be prepared in a known manner (J. Am. Chem. Soc. 2465 /1949/). When the pure erythro or threo isomer is applied as starting substance, it can be prepared preferably from the sodium salt of the isomeric mixture (German Pat. No. 1,064,937), or the pure isomers can be prepared directly in a single step by reacting benzaldehyde with nitroethanol in the presence of an alkali hydroxide catalyst. This latter method is the most preferred one to obtain the pure isomers of the formula (II) compound.

The compounds of the general formula (I) and mixtures thereof possess strong fungicidal and acaricidal activities without exerting, however, any harmful phytotoxic effect. For certain insects a considerable antifeedent effect can also be observed; thus, for example, winged migratory locusts do not consume plants sprayed with the compositions according to the invention. The compositions according to the invention also possess considerable aphicidal effects. Furthermore, they accelerate the germination of certain cultivated plants and also stimulate the dry substance accumulation. The compositions according to the invention, when applied to the plants prior to emergence in the dosages tested, stimulated the dry substance accumulation of the plants and increased their germination abilities; on the other hand, when applied after emergence, they did not show any positive or negative phytotoxic effect.

Based on the test results the compositions according to the invention are active against the following fungus strains: *Alternaria tenuis, Fusarium graminearum, Trichotecium roseum, Aspergillus flavus, Penicillium species, Rhizopus nigricans, Phytophtora infestans, Monilia fructigena, Cladosporium herbarum, Fusarium oxysporum, Aspergillus oryzae, Mucor mucedo, Botrytis cinerea* and *Endostigme pirina.*

The biological effects of the compositions according to the invention were tested primarily on the following plant types: wheat, maize, sorghum, mustard, sunflower, potato, pea and other cultivated plants.

The tests were performed as follows:

Soil samples were layered into culture pots, and an appropriate amount of seeds (in the testing of wheat, maize, sorghum, sunflower, mustard and pea 100 seeds per pot) was sown into the soil. The active agent was applied to the soil either prior to or after plant emergence. The active agents of the general formula (I) were applied in a dosage corresponding to 6 kg/acre. Some of the pots were not treated; these served as controls. Optimum conditions were provided for germination, and the percentage germination, the heights of the 14 days' old seedlings, furthermore their green and dry weights were determined.

In a test series the plants were treated prior to plant emergence with a threo-erythro mixture of 1-phenyl-2-nitro-1,3-propanediol diacetate ground to a particle size of 1 to 20μ (a composition prepared according to Example 14). In two further test series the treatments were performed after plant emergence with a composition prepared according to Example 15 or 16, containing a threo-erythro mixture of 1-phenyl-2-nitro-1,3-propanediol diacetate as active principle. The results are listed in Table 1.

Table 1

| Treatment | Plant | Germination, %[x] | Height, %[x] | Green weight, %[x] |
|---|---|---|---|---|
| pre-emergent | wheat | 63 | 105.5 | 105 |
| | maize | 108 | 99 | 107 |
| | sorghum | 111 | 110 | 120 |
| | mustard | 116 | 104 | 121 |
| | sunflower | 108 | 98 | 120 |
| | pea | 100 | 118 | 131 |
| post-emergent | wheat | — | — | 130 |
| | maize | — | — | 125 |
| | flax | — | — | 130 |
| | capsicum | — | — | 130 |
| | tomato | — | — | 120 |

[x]Control = 100%

Erythro-1-phenyl-2-nitro-1,3-propanediol diacetate, a compound prepared as described in Examples 1, 6 and 7, was dissolved in acetone, and the solution was diluted with water to a final concentration of 0.1 to 1%. The activities of the solutions with varying concentrations were tested against the fungus strains listed in Table 2 by the disc method. The diameters of the colonies developed were measured, and the degree of inhibition was determined in comparison with the values measured for the untreated controls. The degree of inhibition was characterized by a numerical scale ranging from 1 to 4, wherein the individual figures had the following meanings:

1: total inhibition,
2: partial covering,
3: total covering but certain other biological effects (such as morphological changes) can be detected in relation to the controls,
4: no change in relation to the controls.

The results are summarized in Table 2.

Table 2

| Fungus strain | Erythro diacetate 0.1% | 0.3% | 0.5% | 1% | Delan 0.1% | Difolpet 0.1% | Control |
|---|---|---|---|---|---|---|---|
| Botrytis cinerea | 1 | 1 | 1 | 1 | 3 | 1 | 4 |
| Cladosporium herbarum | 1 | 1 | 1 | 1 | 3 | — | 4 |
| Fusarium oxysporum | 2 | 1 | 1 | 1 | 4 | 1 | 4 |
| Penicillium species | 2 | 1 | 1 | 1 | 3 | — | 4 |
| Aspergillus oryzae | 2 | 1 | 1 | 1 | 3 | — | 4 |
| Alternaria tenuis | 2 | 2 | 1 | 1 | — | 1 | 4 |

Delan: 2,3-dicyano-1,4-dithia-anthraquinone
Difolpet: N-(1,1,2,2-tetrachloroethylthio)-4-cyclohexene-1,2-dicarboximide The results of some additional tests are summarized in Tables 3 to 7.

Table 3

| Compound (formulation) | Concentration of the spray solution, % | Test organism | Mortality % |
|---|---|---|---|
| A compound of Ex. 1, 6 and 7 (wettable powder with 50% | 0.02 | Tetrahychus urticae | 4.6 |
| | 0.2 | | 76.0 |
| | 2.0 | | 100.0 |

Table 3-continued

| Compound (formulation) | Concentration of the spray solution, % | Test organism | Mortality % |
|---|---|---|---|
| active agent content) | | | |
| Compounds of Ex. 3 to 6 (wettable powder with 50% active agent content) | 0.02 | " | 13.5 |
| | 0.2 | | 88.8 |
| | 2.0 | | 97.3 |
| Diazinon, Fenkapton | 0.2 | " | 100.0 |
| Compounds of Ex. 1 to 8 | 2.0 | Megaurea vicae | 88.0 |
| | 2.0 | | 70.0 |
| Dimethoate | 2.0 | " | 100.0 |
| Compound of Ex. 9 (powder, 1 to 20 μ) | 0.01 | Acyrthosiphon (leaf aphid) | 35[x] |
| | 0.1 | | 95[x] |
| | 1.0 | | 100[x] |
| | 0.01 | | 90[xx] |
| | 0.1 | | 100[xx] |
| | 1.0 | | 100[xx] |
| Methyl parathione | 0.5 | " | 100[x] |
| | 0.5 | | 100[xx] |

[x]after 24 hours
[xx]after 48 hours
Diazinon: 0,0-diethyl-0-2-isopropyl-4-methyl-6-pyrimidyl-thiophosphate
Fenkapton: S-(2,5-dichlorophenylthiomethyl)-0,0-diethyl-di-thiophosphate
Dimethoate: dimethyl S-(N-methyl-carbamoylmethyl)-di-thiophosphate
Methyl parathione: 0,0-dimethyl-0-(p-nitrophenyl)-thiophosphate Table 4

| Compound (formulation) | Concentration of the spray solution, % | Test organism | Antifeedent effect |
|---|---|---|---|
| Compounds of Ex. 1 to 8 (wettable powder with 50% active agent content) | 0.1 | Indian winged locusts | Did not touch the plant |
| | 0.3 | " | " |
| None (control) | 0.0 | " | Consumed the plant |

Table 5

| Compound (formulation) | Conc. | Test organism | Inhibition of spore germination 0.1% | 1.0% |
|---|---|---|---|---|
| Compound of Ex. 2 (wettable powder with 50% active agent) content) | 0.1% 1.0% | Alternaria tenuis | partial | total |
| | | Fusarium graminearum | partial | total |
| | | Trichotecium roseum | partial | total |
| | | Apergillus flavus | partial | total |
| | | Penicillium species | partial | total |
| | | Rhizopus nigricans | partial | total |
| | | Botrytis cinerea | none | partial |
| | | Phytophtora infestans | partial | total |
| | | Endostigme pirina | partial | total |
| | | Monilia fructigena | none | total |

Conc. = concentration of the spray solution, %

Table 6

| Compound (formulation) | Conc. | Test organism (substrate) | Infection % |
|---|---|---|---|
| Compound of Ex. 2 (wettable powder containing 50% of active agent) | 0.05 | Phytophtora infestans (potato leaves) | 5.0 |
| | 0.1 | | 0.0 |
| | 1.0 | | 0.0 |
| Zineb (wettable powder containing 80% of active agent) | 0.3 | " | 20.0 |
| Untreated control | 0.0 | " | 100.0 |
| Compound of Ex. 2 (wettable powder | | Phytophthora infestans | |

Table 6-continued

| Compound (formulation) | Conc. | Test organism (substrate) | Infection % |
|---|---|---|---|
| containing 50% of active agent | 0.1 | (potato slices)[x] | 0.0 |
| Compound of Ex. 2 (wettable powder containing 50% of active agent) | 0.01<br>0.1<br>1.0 | Fusarium (potato leaves) | 26<br>0<br>0 |
| Zineb (wettable powder containing 80% of active agent) | 0.1 | " | 40 |
| Untreated control | 0.0 | " | 50 |
| Compound of Ex. 9 (wettable powder containing 50% of active agent) | 0.1 | Phytophthora infestans (potato leaves) | 0 |
| Orthocid | 0.2 | " | 0 |
| Untreated control | 0.0 | " | 60 |
| Compound of Ex. 9 | 0.1 | Phytophthora infestans (potato slices)[x] | 0 |

[x]infected under experimental conditions
Conc. = concentrations of the spray solution, %
Zineb: zinc-ethylenebis (thiocarbamate)
Orthocid: N-(trichloromethylthio)-4-cyclohexene-1,2-dicarboximide Table 7

| Compound (formulation) | Concentration of the spray solution, % | Test organism | Inhibition of spore germination | | Activity[x] % | |
|---|---|---|---|---|---|---|
| | | | 0.1% | 1.0% | 0.1% | 1.0% |
| Compound of Ex. 9 (wettable powder containing 50% of active agent) | 0.1% and 1.0% | Alternaria tenuis | total | total | 111 | 333 |
| | 0.1% and 1.0% | Fusariun graminearum | total | total | 300 | 833 |
| | 0.1% and 1.0% | Trichotecium roseum | total | total | 90 | 300 |
| | 0.1% and 1.0% | Aspergillus flavus | total | total | 150 | 466 |
| | 0.1% and 1.0% | Penicilliun species | total | total | 112 | 275 |
| | 0.1% and 1.0% | Botrytis cinerea | total | total | 166 | 316 |
| | 0.1% and 1.0% | Rhizopus nigricans | partial | total | 0 | 170 |
| | 0.1% and 1.0% | Mucor mucedo | partial | total | 0 | 266 |

[x]The activity of a 0.2% solution of Zineb (wettable powder containing 30% of active agent) was regarded as 100%

The invention is elucidated in detail by the aid of the following non-limiting Examples.

EXAMPLE 1

Preparation of erythro-1-phenyl-2-nitro-1,3-propanediol diacetate 158 g. of 1-phenyl-2-nitro-1,3-propanediol sodium salt are introduced within 25 minutes into 700 ml. of stirred glacial acetic acid at a temperature not exceeding 20° C. Thereafter 304 ml. of acetyl chloride are added to the mixture within 35 minutes at a temperature below 20° C. The reaction mixture is stirred for 14 hours at 40° C., and the separated sodium chloride is filtered off. The filtrate is diluted with 600 ml. of petroleum ether and stirred for 2 hours under cooling with ice water. The separated crystalline substance is filtered off. 55 g. (25.6%) of erythro-1-phenyl-2-nitro-1,3-propanediol diacetate are obtained; m.p.: 81°-82° C.

The mother liquor is evaporated. 110.2 g. (51%) of 1-phenyl-2-nitro-1,3-propanediol diacetate are obtained in the form of a threo-erythro isomeric mixture; m.p.: 55°-61° C.

The obtained compounds can be applied for plant protection purposes either separately or in admixture with each other.

EXAMPLE 2

Preparation of threo-1-phenyl-2-nitro-1,3-propanediol diacetate 10 g. of threo-1-phenyl-2-nitro-1,3-propanediol are added slowly into 16 ml. of acetyl chloride at room temperature. Warming and a vigorous development of hydrochloric acid takes place. The cooling of the mixture is controlled so that its temperature does not exceed 40° C. When the development of hydrochloric acid subsides the mixture is stirred at 40° C. for additional 3 hours, thereafter it is allowed to stand at room temperature overnight.

The reaction mixture is diluted with a great amount of petroleum ether and cooled to 0° C. The separated crystalline substance is filtered off and washed with petroleum ether until the wash does not give acidic reaction. In this way 10.4 g. (73%) of threo-1-phenyl-2-nitro-1,3-propanediol diacetate are obtained; m.p.: 72°-73° C.

EXAMPLE 3

Preparation of threo-1-phenyl-2-nitro-1,3-propanediol diacetate 10 g. of threo-1-phenyl-2-nitro-1,3-propanediol are dissolved in 30 ml. of glacial acetic acid and 16 ml. of acetyl chloride are added to the solution at room temperature. The reaction mixture is maintained at 40° C. for 3 hours, thereafter it is allowed to stand at room temperature overnight. The product is precipitated with a great amount of petroleum ether under cooling (0° C.), and the mixture is allowed to stand in a refrigerator for some hours. 11.5 g. (80.5%) of threo-1-phenyl-2-nitro-1,3-propanediol diacetate are obtained; m.p.: 70°-72° C.

EXAMPLE 4

Preparation of threo-1-phenyl-2-nitro-1,3-propanediol diacetate 35 g. of threo-1-phenyl-2-nitro-1,3-propanediol are dissolved in 49 ml. of acetic anhydride, and 49 ml. of acetyl chloride are added to the solution at such a rate that the temperature of the mixture does not exceed 40° C. The mixture is maintained at 40° C. for 8 hours, thereafter it is allowed to stand overnight. The mixture is poured into 200 g. of crushed ice under stirring. A thick oil separates which crystallizes within a short time. The mixture is maintained at 0° C. for 2 hours, thereafter the crystals are filtered off and washed acid-free with cold distilled water. In this way 49.05 g.

(97.5%) of threo-1-phenyl-2-nitro-1,3-propanediol diacetate are obtained; m.p.: 71°–72° C.

24.0 g. of the above product are dissolved in 72 ml. of isopropanol at a temperature of about 85° to 90° C., and the solution is allowed to stand at room temperature. The crystalline product separates within some hours. The crystals are filtered off and washed with cold petroleum ether. 22.19 g. (92%) of purified threo-1-phenyl-2-nitro-1,3-propanediol diacetate are obtained; m.p.: 72°–73° C.

EXAMPLE 5

Preparation of threo-1-phenyl-2-nitro-1,3-propanediol diacetate 19.7 g. of threo-1-phenyl-2-nitro-1,3-propanediol are dissolved in 30 ml. of acetic anhydride, and 0.2 ml. of boron trifluoride etherate are added to the solution in such a way that its temperature does not exceed 20° C. The mixture is stirred at 40° C. for one hour and then it is poured onto ice. The separated crystals are filtered off and washed with ice-cold distilled water. 26.2 g. (93.2%) of threo-1-phenyl-2-nitro-1,3-propanediol diacetate are obtained; m.p.: 69°–71° C.

21.0 g. of the above compound are recrystallized from 50 ml. of ethanol. 16.8 g. (80.0%) of the purified substance are obtained; m.p.: 70.5°–72° C.

EXAMPLE 6

Preparation of erythro-1-phenyl-2-nitro-1,3-propanediol diacetate 4.9 g. of erythro-1-phenyl-2-nitro-1,3-propanediol are dissolved in 14.7 ml. of glacial acetic acid, and 7.85 ml. of acetyl chloride are added to the solution at room temperature. The mixture is maintained at 40° C. for 6 hours, thereafter it is allowed to stand at room temperature overnight. A great amount of petroleum ether is added to the solution, and the mixture is kept in a refrigerator for 4 hours. The separated crystals are filtered off and washed with petroleum ether. 3.08 g. (44%) of erythro-1-phenyl-2-nitro-1,3-propanediol diacetate are obtained; m.p.: 81° C.

EXAMPLE 7

Preparation of erythro-1-phenyl-2-nitro-1,3-propanediol diacetate 8.0 g. of erythro-1-phenyl-2-nitro-1,3-propanediol are dissolved in 11.2 ml. of acetic anhydride, and 11.2 ml. of acetyl chloride are added dropwise to the solution at a temperature not exceeding 40° C. The mixture is maintained at 40° C. for additional 8 hours, thereafter it is poured onto 30 g. of crushed ice with stirring. The product separates slowly. The mixture is maintained at 0° C. for 2 hours, thereafter the product is filtered off and washed acid-free with cold (0° C.) distilled water. The resulting 11.75 g. of crude erythro-1-phenyl-2-nitro-1,3-propanediol diacetate are recrystallized from 66 ml. of ethanol. The crystals are filtered off and washed with petroleum ether. 4.7 g. (41%) of pure erythro-1-phenyl-2-nitro-1,3-propanediol are obtained; m.p.: 79°–80° C.

EXAMPLE 8

Preparation of threo-1-phenyl-2-nitro-1,3-propanediol dipropionate 19.7 g. of threo-1-phenyl-2-nitro-1,3-propanediol are added slowly into 40 ml. of propionic anhydride containing 0.2 ml. of boron trifluoride etherate. The mixture is stirred at 40° C. for 2 hours and then it is poured onto crushed ice. The separated crystals are filtered off and washed with ice-cold distilled water. 28.6 g. (92.6%) of crude threo-1-phenyl-2-nitro-1,3-propanediol dipropionate are obtained. After recrystallization from ethanol 25.25 g. (88.5%) of pure substance are obtained; m.p.: 48°–50° C.

EXAMPLE 9

Preparation of threo-1-phenyl-2-nitro-1,3-propanediol dibenzoate 19.7 g. of threo-1-phenyl-2-nitro-1,3-propanediol are added slowly into 28 g. (24.1 ml.) of benzoyl chloride at such a rate that the temperature of the mixture does not exceed 20° C. Thereafter the mixture is warmed to 85° to 90° C. and maintained at this temperature for 7 to 8 hours. The mixture is allowed to stand at room temperature overnight and then it is diluted with ether. The separated product is filtered off and washed acid-free with petroleum ether. 19.6 g. (48.5%) of crude threo-1-phenyl-2-nitro-1,3-propanediol dibenzoate are obtained. After recrystallization from a mixture of ethanol and tetrahydrofuran 15.8 g. (80.5%) of pure substance are recovered; m.p.: 130.5°–132° C.

EXAMPLE 10

Preparation of threo-1-phenyl-2-nitro-1,3-propanediol dipalmitate

A mixture of 10 g. of threo-1-phenyl-2-nitro-1,3-propanediol and 55.8 g. of palmitoyl chloride is stirred at 80° C. for 8 hours. The reaction mixture is allowed to cool and admixed with petroleum ether. After a short period of standing the separated crude product is filtered off, washed with petroleum ether and recrystallized once from ethanol. 9.95 g. (29.3%) of threo-1-phenyl-2-nitro-1,3-propanediol dipalmitate are obtained; m.p.: 51°–53° C.

EXAMPLE 11

Preparation of threo-1-phenyl-2-nitro-1,3-propanediol bis(phenylacetate)

A mixture of 4.0 g. of threo-1-phenyl-2-nitro-1,3-propanediol and 9.4 g. of phenylacetyl chloride is stirred at 70° C. for 5 hours and then at 85° C. for 10 hours.

The reaction mixture is allowed to cool, poured onto crushed ice, and allowed to stand overnight. The separated thick, oily product is isolated from the aqueous phase and dissolved in 15 ml of diethyl ether. The ethereal solution is dried over magnesium sulfate and filtered. The filtrate is diluted with 25 ml. of petroleum ether and the mixture is allowed to stand for some days. The separated crystalline crude product (5.6 g.) is filtered off, triturated with 15 ml. of ethanol, and the mixture is allowed to stand in a refrigerator overnight. The crystals are filtered off and washed with cold ethanol. The resulting crude product is recrystallized from 12.5 ml. of ethanol. The crystals are filtered off and washed with cold ethanol and petroleum ether. 4.1 g. (46.6%) of threo-1-phenyl-2-nitro-1,3-propanediol bis(phenylacetate) are obtained; m.p.: 63°–64° C.

EXAMPLE 12

Preparation of threo-1-phenyl-2-nitro-1,3-propanediol bis(p-chlorobenzoate)

A mixture of 1.95 g. of threo-1-phenyl-2-nitro-1,3-propanediol and 5.35 g. of p-chlorobenzoyl chloride is stirred at 85° to 90° C. for 14 hours. The mixture is allowed to cool, admixed with ice, and allowed to stand overnight. The separated product is filtered off, washed with water and petroleum ether, and crystallized from 62 ml. of ethanol. 1.08 g. (23.4%) of threo-1-phenyl-2-nitro-1,3-propanediol bis(p-chlorobenzoate) are obtained; m.p.: 107°–109° C.

EXAMPLE 13

Preparation of a wettable powder

The formula (I) active agent is powdered in a micronizer until at least 80% of the substance has the particle size of 1 to 20μ. The powder is homogenized with 1 to 5% by weight of a neutral or non-basic wetting agent and 20 to 60% by weight of a solid inert binding agent (such as kaoline or bentonite). The resulting wettable powder contains about 60 to 82% by weight of active agent.

EXAMPLE 14

Preparation of a wettable powder

One proceeds as described in Example 13 with the difference that 10 to 20% by weight of a stability-increasing acidic buffer substance (such as potassium or sodium dihydrophosphate, lactic acid, tartaric acid, etc.) are also added to the composition during the micronizing and homogenization steps. The resulting wettable powder contains about 54 to 76% by weight of active agent.

EXAMPLE 15

Preparation of a spray composition

The formula (I) active agent is dissolved in benzene or a homologue thereof (such as toluene or xylene) to form a 0.1 to 1% solution. 1 to 3% of a wetting agent and 1% of a stickener are added to the solution, and the solution is filled into aerosol containers equipped with fine spray nozzles using a propellant gas (such as a freon gas, a mixture of propane and butane, carbon dioxide, etc.).

EXAMPLE 16

Preparation of an emulsifiable concentrate

The formula (I) active agent is powdered until at least 80% of the substance has the particle size of 1 to 20μ, and the powdery substance is admixed with an equal weight of an inert organic solvent (such as petrol, xylene, diglyme, etc.) and 5 to 7% of a wetting agent. The resulting emulsifiable concentrate contains about 47 to 48% by weight of active agent. The concentrate can be diluted to any desired concentration with the inert organic solvent applied.

EXAMPLE 17

Preparation of microgranules

The formula (I) active agent is dissolved in chloroform (or in another chlorinated hydrocarbon). The solution, the concentration of which corresponds to the homogenizing technique applied, is applied onto the surface of a granular solid support (such as pearlite, coke powder, etc.; particle size: 0.1 to 1 mm.) according to the "wet" method. Microgranules containing 10 to 30% by weight of active agent are prepared.

What we claim is:

1. A plant protecting composition with fungicidal, acaricidal, aphicidal and insect antifeedent effects, containing an effective amount of a compound of the formula

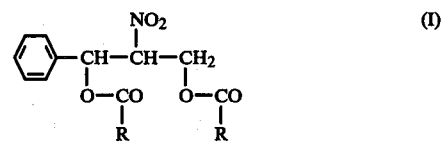

wherein R is a $C_{1-20}$ alkyl group, and a diluent in an amount necessary to make up the final weight of the composition.

2. A method of killing fungi, acarids and aphids and of protecting plants against feeding by insects, comprising applying to growing plants, either prior to or after emergence, an effective amount of a compound having the formula

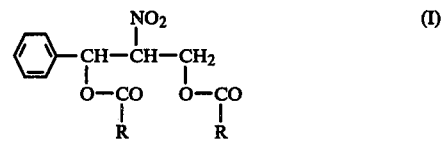

wherein R is a $C_{1-20}$ alkyl group.

* * * * *